United States Patent

Theriot et al.

[11] Patent Number: 5,929,297
[45] Date of Patent: Jul. 27, 1999

[54] OLEFIN OLIGOMERIZATION PROCESS

[75] Inventors: Kevin J. Theriot, Baton Rouge; Robert G. Irwin, Prairieville, both of La.

[73] Assignee: BP Amoco Corporation, Chicago, Ill.

[21] Appl. No.: 08/936,410

[22] Filed: Sep. 25, 1997

Related U.S. Application Data

[63] Continuation of application No. 08/575,948, Dec. 20, 1995, abandoned.

[51] Int. Cl.$^6$ .................................. C07C 2/04; C07C 2/02
[52] U.S. Cl. ........................... 585/525; 585/510; 585/520; 585/527
[58] Field of Search ...................................... 585/510, 520, 585/525, 527

[56] References Cited

U.S. PATENT DOCUMENTS

| | | | |
|---|---|---|---|
| 4,409,415 | 10/1983 | Morganson et al. | 585/525 |
| 4,902,846 | 2/1990 | DiLeo et al. | 585/525 |
| 4,935,570 | 6/1990 | Nelson et al. | 585/329 |
| 4,950,822 | 8/1990 | DiLeo et al. | 585/310 |
| 4,956,512 | 9/1990 | Nissfolk et al. | 585/521 |
| 5,068,487 | 11/1991 | Theriot | 585/510 |
| 5,225,588 | 7/1993 | Senaratne et al. | 560/71 |
| 5,241,085 | 8/1993 | Senaratne et al. | 549/396 |
| 5,250,750 | 10/1993 | Shubkin et al. | 174/17 LF |
| 5,302,772 | 4/1994 | Sowerby et al. | 585/532 |
| 5,320,993 | 6/1994 | Wu | 502/103 |
| 5,376,612 | 12/1994 | Reagen et al. | 502/104 |
| 5,491,272 | 2/1996 | Tanaka et al. | 585/520 |

*Primary Examiner*—Glenn Caldarola
*Assistant Examiner*—Thuan D. Dang
*Attorney, Agent, or Firm*—James R. Henes; Stephen L. Hensley

[57] ABSTRACT

Alpha-olefin oligomers are produced by oligomering alpha-olefin monomer with a catalyst system comprising boron trifluoride, a protic promoter, and a special type of modifier. The modifier is a compound that satisfies the following criteria: (a) it has at least one moiety in which a carbonyl group is directly bonded to a nitrogen atom which is in turn bonded to two separate carbon atoms, (b) it is devoid of any nitrogen atom other than a nitrogen atom that is either (i) directly bonded to two separate carbon atoms and to a carbonyl group or (ii) is triply bonded to a single carbon atom, and (c) it is devoid of any protonic functional substituent. These modifiers control the oligomer product distribution and provide higher percentages of lower oligomers, especially dimers.

18 Claims, No Drawings

OLEFIN OLIGOMERIZATION PROCESS

This is a continuation of application Ser. No. 08/575,948 now abandoned, filed Dec. 20, 1995.

TECHNICAL FIELD

This invention relates generally to the preparation of alpha-olefin oligomers which are useful as synthetic lubricants and functional fluids. More particularly, this invention relates to $BF_3$-promoter catalyst systems which use a modifier to control the oligomer product distribution and provide higher percentages of lower oligomers, especially dimers.

BACKGROUND

Alpha-olefin oligomers and their use as synthetic lubricants are well-known. The oligomers are usually hydrogenated in order to improve their stability. Early reports of such oligomeric synthetic lubricants appear in Seger et al. U.S. Pat. No. 2,500,161 and Garwood U.S. Pat. No. 2,500,163.

Oligomerization of alpha-olefins in a Group IV metal oxide bed using a $BF_3$-protic promoter catalyst is described in U.S. Pat. No. 2,766,312. Promoters referred to therein include water, carboxylic acid, alkyl halides, alcohols and ethers.

U.S. Pat. No. 2,806,072 discloses the dimerization of $C_6$–$C_{12}$ polypropylenes using a preformed $BF_3$-dialkyl ether catalyst.

Oligomerization of olefins using $BF_3$-promoter catalyst complexes of acid anhydrides, esters, ketones and aldehydes is described in U.S. Pat. No. 3,382,291.

U.S. Pat. No. 3,769,363 to Brennan discloses oligomerization of $C_6$–$C_{12}$ normal alpha-olefins, such as 1-decene, with $BF_3$ and $C_5$ carboxylic acid to improve trimer yields.

U.S. Pat. No. 3,997,621 also to Brennan describes oligomerization of $C_6$–$C_{12}$ normal alpha-olefins with $BF_3$ using alcohols or water promoters in conjunction with small amounts of methyl and ethyl esters of a $C_2$–$C_5$ monocarboxylic acid to improve trimer yields.

In U.S. Pat. No. 4,172,855 $BF_3$-promoter catalysts for grafting a second alpha-olefin onto a $C_6$–$C_{12}$ alpha-olefin dimer to form a low volatility lubricating oil is described. The promoters include glycol ethers such as ethylene glycol monomethyl ether and propylene glycol monoethyl ether, and diisobutyl ether.

U.S. Pat. No. 4,218,330 to Shubkin describes dimerization of $C_{12}$–$C_{18}$ alpha-olefin monomer with a $BF_3$-water complex and an excess of $BF_3$. Unreacted monomer is distilled from the reaction product leaving mainly dimer with minor amounts of trimer and higher oligomers. The product is hydrogenated for use as a lubricant.

U.S. Pat. No. 4,436,947 to Morganson et al. discloses oligomerization of $C_6$–$C_{20}$ olefins, such as 1-decene, with $BF_3$ and a mixture of an aliphatic alcohol, an aliphatic ketone, and a polyol. The product is mainly trimer.

U.S. Pat. No. 4,982,026 to Karn describes polymerization of $C_2$–$C_6$ alkene monomers with $BF_3$ and a strong acid, such as phosphoric acid to produce a polymer having a molecular weight of from 250 to 500 and having a high vinylidene content.

U.S. Pat. No. 5,068,487 describes a process for producing products containing predominately dimers and trimers of alpha-olefins using a $BF_3$ catalyst promoted by an alcohol alkoxylate.

U.S. Pat. No. 5,191,140 discloses a process for making alpha-olefin oligomers by use of $BF_3$ promoted by at least two of water, alcohols and anhydrides to peak the reaction at lower molecular weight product.

U.S. Pat. No. 5,396,013 indicates that polyethers will moderate promoted $BF_3$-catalyzed oligomerizations to provide either predominately dimer- or trimer-containing oligomers.

U.S. Pat. No. 5,420,373 discloses a process for producing predominately dimer and trimer from $C_6$–$C_{20}$ olefins, such as 1-decene, with $BF_3$ and a hydroxy carbonyl promoter—i.e., a hydroxy ketone or a hydroxy aldehyde. Secondary promoters may also be used, namely aldehydes, alcohols, alcohol alkoxylates, carboxylic acids, ethers, ketones, and their mixtures.

The particular application for which the oligomer oils are used depends largely upon their viscosity, with viscosities of about 2–10 cSt at 100° C. being preferred for general lubricating oil applications. These materials are, in general, mixtures of different percentages of dimer, trimer, tetramer, pentamer and, in the case of the higher viscosity products in this range, higher oligomers as well. To increase viscosity, processes are used which either produce more of the higher oligomers or some of the lower oligomers are removed such as by distillation.

Most lower viscosity dimer products are obtained as by-products of the production of higher viscosity synthetic oils. Because of increasing use of dimers in applications such as low temperature lubricants and drilling fluids, methods for their preferential production are of particular interest. Although higher oligomerization temperatures tend to increase dimer formation, use of such higher temperatures can cause corrosion of process equipment.

SUMMARY OF THE INVENTION

New, highly effective modifiers for $BF_3$-catalyzed oligomerization reactions have been discovered. By the practice of preferred embodiments of this invention it has been found possible to modify the promoted catalytic reaction so that product containing as much as about 50% or more of dimer can be produced at modest reaction temperatures. Additionally, it has been found possible to produce an oligomer product mixture composed almost entirely of dimer and trimer. For example, apart from unreacted monomer, a product mixture containing 98.6% of dimer and trimer and only 1.4% of higher oligomer (all tetramer) has been produced by use of this invention. Moreover, 78% of this dimer/trimer mixture was dimer.

The modifiers employed pursuant to this invention have a particular chemical configuration which enables them to exert a profound beneficial effect upon the oligomerization reaction. This particular configuration involves compounds that are characterized (i) by having at least one moiety in which a carbonyl group is directly bonded to a nitrogen atom which is in turn bonded to two separate carbon atoms, and (ii) by being devoid of any nitrogen atom other than a nitrogen atom that is directly bonded to two separate carbon atoms and to a carbonyl group or is triply bonded to a single carbon atom (i.e., is the nitrogen atom of a cyano, cyanate or thiocyanate group). Preferred compounds of this type can be represented by the general formula

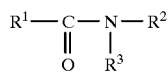

(I)

where $R^1$ is a hydrogen atom, a hydrocarbyl group, a hydrocarbyloxy group, a heterocyclic group having at least a 5-membered ring and from 1 to 2 hetero atoms each of which is, independently, an oxygen or a nitrogen atom; $R^2$ and $R^3$ are, independently, hydrocarbyl groups or acyl groups; and wherein either (a) $R^1$ and $R^2$ taken together can be a single divalent group forming at least a 5-membered heterocyclic group which includes the depicted nitrogen atom and from 1 to 2 carbonyl groups or (b) $R^2$ and $R^3$ taken together can be a single divalent group forming at least a 5-membered heterocyclic group which includes the depicted nitrogen atom; all with the proviso that every other nitrogen atom, if any, in the molecule other than that depicted is directly bonded to a carbonyl group and to two other separate carbon atoms or is in a cyano, cyanate or thiocyanate group. In addition, the modifier is devoid of any protonic functional substituent. Typical compounds of formula (I) above include amides, ureas, thioureas, imides, carbamates, thiocarbamates, and like compounds as long as they satisfy the structural criteria set forth in connection with formula (I).

It is to be clearly understood that in identifying the structure or identity of the olefin, the protonic promoter and the modifier, the structure or identity represents the structure or identity of the respective compounds as they are charged or added to or introduced into the reaction mixture or reaction zone. It matters not what transformations (chemical or otherwise) may occur once the compounds have been contacted with one or more of the other compounds so long as the end result is that oligomerization of the olefin occurs. Thus this specification and the claims hereof are to be interpreted with reference to the structure and identity of these components as they are charged to the reactor and not with reference to their structure or identity once two or more of them have been brought together in the reactor. For the purposes of this invention it is wholly immaterial and irrelevant whether one or more of such components lose their original identity or chemical structure before or during the process, provided only that oligomerization of the olefin takes place.

Accordingly, in one of its embodiments this invention provides a process of preparing alpha-olefin oligomer which comprises contacting an alpha-olefin monomer which contains from about 6 to about 20 carbon atoms with a catalyst system comprising boron trifluoride, a protic promoter, and a modifier of this invention.

In a preferred embodiment the foregoing process is conducted under oligomerization conditions forming a reaction mixture that contains 40% or more of dimer, terminating the oligomerization in said reaction mixture, and recovering the dimer from said reaction mixture, for example, by distillation. The process can produce mixtures containing over 40% of dimer, over 60% of combined dimer and trimer, and less than 20% of higher oligomer. Indeed, it has been found possible to conduct the process whereby oligomerization reaction product mixtures can be formed containing over 40% of dimer, over 60% of combined dimer and trimer, and less than 2% of higher oligomer, and this constitutes a particularly preferred embodiment of this invention.

Another preferred embodiment utilizes water and/or at least one alkanol as the catalyst promoter in the each of the foregoing processes.

Still another preferred embodiment involves conducting a process of this invention using as the protic promoter an alcohol alkoxylate such as described in U.S. Pat. No. 5,068,487.

The above and other embodiments and features of this invention will become still further apparent from the ensuing description and appended claims.

FURTHER DESCRIPTION

The olefins used in making the oligomers are predominately (at least 50 mole %) $C_6$–$C_{20}$ straight chain (i.e., linear) monoolefinically unsaturated hydrocarbons in which the olefinic unsaturation exists in the 1- or alpha-position of the straight chain. Such alpha-olefins are available as articles of commerce, and can be made by thermal cracking of paraffinic hydrocarbons or by well-known Ziegler ethylene chain growth technology. Individual olefins can be used as well as mixtures of such olefins. Examples of olefins that can be used are 1-hexene, 1-heptene, 1-octene, 1-nonene, 1-decene, 1-undecene, 1-dodecene, 1-tridecene, 1-tetradecene, 1-hexadecene, 1-octadecene, 1-eicosene, and mixtures of two or more of such 1-olefins. Remotely branched 1-olefins such as 5-methyl-1-heptene, 6-methyl-1-heptene, 6-methyl-1-octene, 7-methyl-1-octene, 6,7-dimethyl-1-octene, 7,7-dimethyl-1-octene, 8-methyl-1-nonene, and like 1-olefins can also be used especially when used together with linear 1-olefins. The more preferred olefins are linear alpha-olefin monomers containing about 8–14 carbon atoms. The most preferred 1-olefin monomer is 1-decene.

Minor amounts of up to about 50, and usually less than 25 mole % of internal and/or vinylidene olefins can be present in the olefin monomers.

Oligomerization is effected by contacting the monomer(s) with a catalytic amount of boron trifluoride, which typically is at least about 0.002 moles per mole of olefin, together with a protic promoter and a modifier. Preferably the reaction is performed in a reaction mixture saturated with boron trifluoride or in a sealed agitated reactor under an atmosphere enriched in boron trifluoride.

Among the protic promoters that can be used are water, carboxylic acids, mineral acids, alcohols, phenols, carboxylic acid esters and anhydrides, ketones, aldehydes, hydroxy ketones, hydroxy aldehydes, alcohol alkoxylates, and mixtures of any two or more of the foregoing. Preferred are water, $C_1$ to $C_{24}$ alcohols and, more preferably, $C_1$ to $C_{12}$ alcohols, and alcohol alkoxylates such as described in U.S. Pat. No. 5,068,487. Examples of preferred alcohols include methanol, ethanol, 1-propanol, 2-propanol, 1-butanol, 2-methyl-1-propanol, 1-pentanol, 2-pentanol, 1-hexanol, 2-hexanol, 1-heptanol, 1-octanol, 2-ethyl-1-hexanol, 1-nonanol, 1-decanol, 1-undecanol, 1-dodecanol, and mixtures of two or more $C_1$ to $C_{12}$ alcohols. Of these, 1-propanol and 1-butanol are particularly preferred. Examples of alcohol alkoxylates include 2-methoxyethanol, 2-ethoxyethanol, 1-methoxy-2-propanol, 4-ethoxy-1-butanol, 2-butoxyethanol, and their analogs and homologs. The protic promoter is used in an oligomerization-promoting amount, i.e., an amount that causes the $BF_3$ to function as an oligomerization catalyst, such as for example from about 0.001 to about 0.04 moles per mole of alpha-olefin monomer(s). In general the $BF_3$ is used in a molar excess relative to the quantity of promoter(s) used, typically by maintaining a pressurized atmosphere of $BF_3$ or $BF_3$ and nitrogen in the reaction vessel. The promoter can be mixed with the olefin feed or the promoter can be charged separately to the reactor, either entirely at the outset or portionwise as the oligomerization proceeds.

Typically the modifiers of Formula (I) will contain up to about 40 carbon atoms in the molecule, and preferably up to about 20 carbon atoms in the molecule. The modifiers may contain additional functionality in the molecule, provided the functionality is such that it does not significantly impair the effectiveness of the modifier. Substituents that do not impair the effectiveness of the modifier and that thus can be present therein are the following: halide, hydrocarbyloxy, hydrocarbylthio, ether oxygen linkage, thioether sulfur linkage, nitro, hydrocarbylsilyl, cyano, cyanate, thiocyanate, carbonyl, and thiocarbonyl. Such substituents are non-protonic functional substituents. It will be appreciated that the hydrogen atom bonded to the carbonyl group of an N,N-dihydrocarbylformamide is not a protonic substituent because of the electronic withdrawal property of the carbonyl group.

In general, the preferred modifiers are those that contain no additional functionality in the molecule.

Suitable amides of formula (I) include amides of mono and polycarboxylic acids such as N,N-dihydrocarbylformamides, N,N-dihydrocarbylacetamides, N.N-dihydrocarbylpropionamides, N,N-dihydrocarbylbutyramides, N,N-dihydrocarbylisobutyramides, and their higher homologs. Each hydrocarbyl group of the N,N-dialkylformamides typically contains up to about 18 carbon atoms and preferably up to about 8 carbon atoms. Particularly preferred are N,N-dimethylformamide and N,N-diethylformamide.

Suitable ureas of formula (I) include compounds having one or more urea linkages in the molecule provided that each nitrogen of such linkages is also directly bonded to two separate carbon atoms, and that there are no nitrogen atoms in the molecule that (a) are not directly bonded to a carbonyl group and to two other separate carbon atoms or (b) are not the nitrogen atom of a cyano, cyanate or thiocyanate group, and that there are no protonic functional substituents in the molecule. Corresponding thioureas can also be employed.

Imides of formula (1) include compounds having one or more imido linkages in the molecule provided that each nitrogen of such linkages is also directly bonded to a separate carbon atom, and that there are no nitrogen atoms in the molecule that are either (a) not directly bonded to a carbonyl group and to two other separate carbon atoms or (b) not the nitrogen atom of a cyano, cyanate or thiocyanate group. Also the imides must be free of any protonic functional substituent.

Carbamates suitable for use as modifiers have at least one carbamate moiety in the molecule, the nitrogen atom of which is also directly bonded to two separate carbon atoms, again with the proviso that (i) there are no nitrogen atoms in the molecule that are (a) not directly bonded to a carbonyl group and to two other separate carbon atoms, or (b) not the nitrogen atom of a cyano, cyanate or thiocyanate group, and (ii) there are no protonic functional substituents in the molecule. Corresponding mono- and dithiocarbamates can also be used.

Compounds meeting the requirements of formula (I) above that contain two or more functional groups or moieties of the modifiers described above can also be used. For example, the modifier may contain in the same molecule an amido and an imino moiety, or a urea and a carbamate moiety, etc., always with the proviso that the compound meets the requirements set forth above in connection with formula (I).

Illustrative examples of suitable modifiers of this invention include: 1-methyl-2-pyrrolidinone, N-methylsuccinimide, N-isopropylphthalimide, N-methylmaleimide, N-methyl-naphthalimide, N-acetyl-2-pyrrolidone, N-acetylsuccinimide, N-acetylphthalimide, N-(bromomethyl)phthalimide, N-(4-acetylphenyl)maleimide, succinimidopropionitrile, 2-methyl-1-pyrrolidinecarboxaldehyde, N-formylpyrrolidine, N-formylmorpholine, N-formylpiperidine, 2-methoxy-1-pyrrolidinecarboxaldehyde, phenyl N,N-dimethylcarbamate, ethyl diphenylcarbamate, N,N-dimethyl-2,4-dichlorophenylcarbamate, ethyl N-(2-chloroethyl)-N-isobutyrylcarbamate, 1,3-dimethyl-2-imidazolidinone, bis(pentamethylene)urea, 1,3-dimethyl-3,4,5,6-tetrahydro-2(1H)-pyrimidinone, 1,1,3,3-tetramethyl urea, 1,1,3,3-tetraphenyl urea, triglycidyl isocyanurate, N-methylformanilide, N-methyldiacetamide, N-ethyl-p-chloroformanilide, N,N-bis(2-cyanoethyl)formamide, N,N-bis(methoxymethyl)formamide, N,N-bis(2-chloroethyl)formamide, and N,N-bis(2,3-difluoropropyl)formamide, and many other similar compounds While normally a single modifier is used in the process of this invention, suitable mixtures of two or more modifiers can be employed, if desired.

In conducting the process of this invention the alpha-olefin or mixture of alpha-olefins, boron trifluoride, protic promoter and modifier can be charged to the reactor in any suitable sequence. Preferably, however, the modifier should be present before any substantial amount of oligomerization has occurred. In this way the maximum beneficial reaction modifying effect of the modifier can be realized.

The reaction can be carried out as a batch, continuous, or semi-continuous process at temperatures which typically are in the range of 0 to 200° C., and preferably in the range of about 30 to about 150° C. More preferably, the temperature is maintained in the range of about 30 to about 60° C., and especially in the range of about 40 to about 60° C. The reaction is typically conducted at pressures ranging from atmospheric up to, for example, 1000 psig, and preferably in the range of about 5 to about 100 psig. The progress of the reaction can be monitored, if desired, by taking samples of the oligomerization mixtures at suitable periods during the course of the reaction and subjecting the sample to gas chromatographic (GC) analysis. In this connection, all references in this specification and in the claims to percentages of oligomer components in the oligomerization reaction product mixture and to olefin conversion percentages are based on GC area percentages in which the analyses are conducted using a Hewlett Packard 5890 gas chromatograph equipped with a flame ionization detector and a methyl siloxane column operated under the following conditions: initial temperature=100° C.; final temperature=350° C.; Rate=15° C./minute.

The reaction can be conducted in a single stirred reactor or in a series of reactors.

To terminate the oligomerization reaction when the desired product distribution and olefin conversion have been achieved, the dimer enriched reaction mixture can be quenched with or in water or an aqueous solution, such as a solution of a salt or a base, or more preferably a solution of a strong base such as sodium hydroxide or potassium hydroxide. The organic phase is recovered and unless the oligomeric product is to be used in the form produced, the reaction product is distilled to recover the product fraction(s) desired. Unreacted olefin can be recovered and recycled.

In most cases the modifiers are used in proportions relative to the promoter that will peak the oligomerization at the dimer stage, but in some cases the proportions can be adjusted for peaking at the trimer stage. Thus in general the ratio of modifier to promoter will usually fall somewhere within the range of from about 0.1 to about 10 moles of modifier per mole of promoter, and typically within the range of from about 0.5 to about 2 moles of modifier per mole of promoter. For producing product highly enriched in dimer, the preferred proportions fall in the range of from about 0.75 to about 1.25 moles of modifier per mole of promoter. It should be understood that one should use a suitable ratio for achieving the particular results desired under the particular reaction conditions and with the particular materials selected for use. Thus the ratio that will best serve the needs of the situation at hand can be determined by performing a few oligomerizations using procedures such as given in the following illustrative example.

EXAMPLE

1-Decene, 1-butanol (1.0 mole % based on 1-decene) and dimethyl formamide modifier (1.0 mole % based on 1-decene) are charged to a reactor equipped with cooling means, stirring means and inlet/outlet ports. The reactor is sealed and pressurized (10 psig) with boron trifluoride, and the temperature of the stirred mixture is maintained at 50° C. by external cooling for 180 minutes. Periodic samples are taken for GC analysis to monitor the progress of the reaction. To terminate the reaction, the reactor is vented into a caustic scrubber, purged with nitrogen, and the reactor contents are drained into 10% aqueous caustic solution. The product is then washed twice with water. The final product mixture is analyzed by GC for product composition. Table I summarizes the results as Run No. 1.

The Control of Table I (Run No. 2) was carried out in the same manner as Run No. 1 except that no modifier was used and the reaction time was 120 minutes. For comparative purposes the results using N-methylformamide and with no promoter, 1-butanol or otherwise, are also given the Table I as Run No. 3.

TABLE I

| Run No. | $C_{20}$, % | $C_{30}$, % | $C_{40}$, % | $C_{50}$, % | Conversion % |
|---|---|---|---|---|---|
| 1 | 49.4 | 13.7 | 0.9 | — | 64.0 |
| 2 | 11.8 | 65.2 | 16.7 | 3.8 | 97.6 |
| 3 | 3.0 | — | — | — | 3.0 |

The entire disclosure of each and every U.S. patent referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of preparing alpha-olefin oligomer which comprises contacting an oligomerizable alpha-olefin monomer with a catalyst system comprising boron trifluoride, a protic promoter, and a compound that:

a) has at least one moiety in which a carbonyl group is directly bonded to a nitrogen atom which is in turn bonded to two separate carbon atoms, b) is devoid of any nitrogen atom other than a nitrogen atom that is either (i) directly bonded to two separate carbon atoms and to a carbonyl group or (ii) is triply bonded to a single carbon atom, and c) is devoid of any protonic functional substituent;

wherein the alpha-olefin is predominately a linear alpha-olefin having from 8 to 14 carbon atoms, and wherein the oligomerization forms a final reaction product mixture that contains over 40% of dimer, over 60% of combined dimer and trimer, and less than 20% of higher oligomer.

2. A process according to claim 1 wherein the protic promoter is water and/or at least one alcohol.

3. A process according to claim 1 wherein the protic promoter is an alcohol alkoxylate.

4. A process according to claim 1 wherein the alpha-olefin is 1-decene.

5. A process according to claim 1 wherein said compound is a compound of the formula $R^1CONR^2R^3$ where $R^1$ is a hydrogen atom or a hydrocarbyl group and $R^2$ and $R^3$ are hydrocarbyl groups.

6. A process according to claim 1 wherein the modifier is N,N-dimethylformamide or N,N-diethylformamide.

7. A process according to claim 1 wherein the protic promoter as charged is an alcohol, wherein the temperature is maintained in the range of about 20 to about 60° C. throughout substantially the entire reaction, and wherein the pressure is maintained in the range of about 5 to about 100 psig throughout substantially the entire reaction.

8. A process of preparing alpha-olefin oligomer which comprises oligomerizing an oligomerizable alpha-olefin monomer with a catalyst system comprising boron trifluoride, a protic promoter, and a modifier, at a temperature in the range of about 0 to about 200° C. and under an atmosphere comprising boron trifluoride at a pressure in the range of about atmospheric to about 1000 psig, said modifier being charged as a compound of the formula

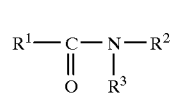

(I)

where $R^1$ is a hydrogen atom, a hydrocarbyl group, a hydrocarbyloxy group, a heterocyclic group having at least a 5-membered ring and from 1 to 2 hetero atoms, each of which is, independently, an oxygen or a nitrogen atom; $R^2$ and $R^3$ are, independently, hydrocarbyl groups or acyl groups; and wherein either (a) $R^1$ and $R^2$ taken together can be a single divalent group forming at least a 5-membered heterocyclic group which includes the depicted nitrogen atom and from 1 to 2 carbonyl groups or (b) $R^2$ and $R^3$ taken together can be a single divalent group forming at least a 5-membered heterocyclic group which includes the depicted nitrogen atom; all with the proviso that (i) no nitrogen atom in the molecule is not directly bonded to a carbonyl group and to two other separate carbon atoms or is not in a cyano, cyanate or thiocyanate group, and (ii) the compound is devoid of any protonic functional substituent, wherein the alpha-olefin monomer as charged is predominately a linear alpha-olefin having from 8 to 14 carbon atoms and wherein the oligomerization forms a final reaction product mixture that contains over 40% of dimer, over 60% of combined dimer and trimer, and less than 20% of higher oligomer.

9. A process according to claim 8 wherein the protic promoter as charged is an alcohol or alcohol alkoxylate or a combination thereof.

10. A process according to claim 8 wherein the alpha-olefin as charged is 1-decene.

11. A process of preparing alpha-olefin oligomer enriched in dimer which comprises oligomerizing a predominately linear alpha-olefin monomer having in the range of 8 to 14 carbon atoms in the molecule with a catalyst system comprising, as charged, (a) boron trifluoride, (b) a protic promoter, and (c) an N,N-dialkylformamide modifier, at a temperature in the range of about 30 to about 150° C., under an atmosphere comprising, as charged, boron trifluoride at a pressure in the range of 5 psig to about 100 psig, and in proportions, as charged, in the range of about 0.5 to about 2 moles of modifier per mole of promoter, that form an oligomerization product mixture containing at least about 40% of dimer, over 60% of combined dimer and trimer and less than 20% of higher oligomer, and terminating the oligomerization in said reaction mixture.

12. A process according to claim 11 wherein the protic promoter, as charged, is water, an alcohol, an alcohol alkoxylate, or any combination of two or more of these.

13. A process according to claim 11 wherein the alpha-olefin monomer, as charged, is 1-decene and the protic promoter, as charged, is an alcohol.

14. A process according to claim 13 wherein the oligomerization is terminated by quenching the said oligomerization product mixture with, as charged, water or an aqueous solution.

15. A process according to claim 14 wherein said proportions, as charged, are in the range of about 0.75 to about 1.25 moles of modifier, as charged, per mole of promoter, as charged.

16. A process according to claim 14 wherein, as charged, said promoter and said modifier are employed in substantially equimolar proportions.

17. A process according to claim 13 wherein the temperature is maintained in the range of about 20 to about 60° C. throughout substantially the entire oligomerization.

18. A process according to claim 17 wherein said proportions, as charged, are in the range of about 0.75 to about 1.25 moles of modifier per mole of promoter.

* * * * *